(12) United States Patent
Ye et al.

(10) Patent No.: US 7,881,779 B2
(45) Date of Patent: Feb. 1, 2011

(54) METHOD AND APPARATUS FOR SYNTHETICALLY DETECTING VENTRICULAR FIBRILLATION

(75) Inventors: Wenyu Ye, Nanshan (CN); Junbiao Hong, Nanshan (CN); Shufeng Li, Nanshan (CN); Shan Lu, Nanshan (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 1061 days.

(21) Appl. No.: 11/607,457

(22) Filed: Dec. 1, 2006

(65) Prior Publication Data

US 2007/0179393 A1    Aug. 2, 2007

(30) Foreign Application Priority Data

Dec. 29, 2005    (CN)    ......... 2005 1 0121438

(51) Int. Cl.
*A61B 5/0402*    (2006.01)
(52) U.S. Cl. ......... 600/518; 607/14
(58) Field of Classification Search ......... 600/515–518; 607/4, 5, 14
See application file for complete search history.

(56) References Cited

U.S. PATENT DOCUMENTS

| 6,308,094 | B1 | 10/2001 | Shusterman et al. | |
| 6,490,478 | B1 * | 12/2002 | Zhang et al. | ......... 600/518 |
| 6,871,089 | B2 | 3/2005 | Korzinov et al. | |

FOREIGN PATENT DOCUMENTS

| CN | 1387823 | 1/2003 |
| CN | 1559341 A | 1/2005 |
| WO | 0224276 A1 | 3/2002 |

* cited by examiner

*Primary Examiner*—Niketa I Patel
*Assistant Examiner*—Rex Holmes
(74) *Attorney, Agent, or Firm*—Kory D. Christensen; Stoel Rives LLP

(57) ABSTRACT

The present application discloses a complexity-based method for synthetically detecting ventricular fibrillation, which centers on complexity calculations while incorporating a plurality of feature values and thus differentiates more effectively among various types of ECG signals. The method further modifies the complexity algorithm, making it more adapted to reflecting characteristics of the VF-related signals, thereby enabling high sensitivity and specificity of detection. Further, the related calculation load is reduced according to the algorithm. As such, the method can fully satisfy the clinical needs and is aimed for solving the problems of low sensitivity, low specificity and weak anti-interference ability present in current medical equipment for detecting ventricular fibrillation, such as monitors, implanted cardioversion defibrillator (ICD), automatic external defibrillator (AED) and so on. Systems for performing the method are also disclosed.

4 Claims, 4 Drawing Sheets

METHOD AND APPARATUS FOR SYNTHETICALLY DETECTING VENTRICULAR FIBRILLATION

RELATED APPLICATION DATA

This application claims priority to Chinese Patent Application No. 200510121438.6, filed on Dec. 29, 2005, Chinese Publication No. 1989897, published on Jul. 4, 2007, the entire disclosure of which is expressly incorporated by reference herein.

FIELD

The present application relates to a method for detecting an electrocardiogram (ECG) signal from body-surface, and in particular to a method and apparatus for detecting ventricular fibrillation (VF).

BACKGROUND

As the ventricular fibrillation morbidity constantly increase over the past ten years or so, while no remarkable improvement has been made in saving lives from the disease, the issues of automatic detection of ventricular fibrillation and defibrillation thereof have drawn increasing attention from all the society. As early as the beginning of 1990s, such cardiology authority as the "American Heart Association" (AHA) appealed for urgent efforts on developing automatic defibrillation facilities.

In view of the detection methods developed in recent years, it can be learned that commonly used at present are a time-field detection method, a frequency-field detection method and a time-frequency analysis detection method, as well as relevant dynamics analysis method and so on.

In particular, the patent document WO0224276, tilted "System and Method for Complexity Analysis-Based Cardiac Tachyarrhythmia Detection" discloses a complexity-based method for detecting ventricular fibrillation as follow.

1. Pass signal through a filter in the range of 3 to 33 Hz;
2. Calculate a heart rate (HR) indicated by the signal;
3. Convert the data into 0 and 1, which comprises:
   (1) obtaining the mean of all the positive R-waves (MPRV) as well as the mean of all the negative R-waves (MNRV) respectively; wherein if no negative R-wave exists, setting MNRV to be 33% of the MPRV (MNRV=33% MPRV), while if no positive R-wave exists, then MPRV to 33% of the MNRV (MPRV=MNRV×33%);
   (2) obtaining the number of samples whose values fall between 10% of MNRV and 10% of MPRV, i.e. Baselinedata; then determining the ratio based on "ratio=Baselinedata/N", wherein N represents the total number of samples;
   (3) if the ratio is smaller than or equal to 20%, setting a threshold Td as 0 (Td=0); if the ratio is larger than 20%, comparing the number of positive R-wave (NPR) to the number of negative R-wave (NNR), wherein if NPR is smaller than NNR, then Td is set to MPRV/2 (Td=MPRV/2); otherwise, Td is set to MNRV/2 (Td=MNRV/2).
   (4) converting the amplitude value sequence $A_1, A_2, \ldots A_N$ of the sampled signal into 0 and 1 base on $T_d$, wherein if $A_i$ is larger than Td, $A_i$ is set as 1; otherwise, it is set as 0 if $A_i <= T_d$.
4. Calculate the complexity of the converted sequence using Lempel-Ziv algorithm:
   (1) Defining a binary character sequence formed of the converted $A_1, A_2, \ldots A_N$ as $S_1, S_2, \ldots S_n$, wherein $S=S_1 S_2 \ldots S_r$, and $Q=S_{r+1}$, $0 \leq r \leq n-1$.
   (2) Designating SQ to represent a general character string formed of two concatenated strings S, Q, and SQV to represent a character string obtained after with the last character of SQ deleted, i.e., $SQV=S_1 S_2 \ldots S_r$. It is determined whether Q is contained in SQV. If Q is not contained in SQV, then $S_{r+1}$ is added to S. In that case, the complexity C(n) increments, and the process proceed to determine the next character $S_{r+2}$. If $Q=S_{r+1}$ is contained in SQV, it is then determined whether $Q=S_{r+1}S_{r+2}$ is contained in SQV, here $SQV=S_1 S_2 \ldots S_r S_{r+1}$. If so, then $Q=S_{r+1}S_{r+2}S_{r+3}$ is further determined.
   (3) Continuing like this, the procedure may result in two possibilities: either that Q contains the last symbol Sn of the originally given sequence so that the analysis is closed, or that if any $Q=S_{r+1}S_{r+2} \ldots S_{r+i}$ is not contained in SQV, then the Q is added to S, $S=S_1 S_2 \ldots S_r S_{r+1} \ldots S_{r+i}$, and the complexity C(n) increments. Thereby, a final result of the complexity C(n) can be calculated. Take the sequence 0011110000111000011111001100011110001 for example. According to the Lempel-Ziv algorithm, Q character strings thereof are defined as 0.01.1110.0001.1100001111.00110.00111100.01 after each determination, with each Q string shown in between every two punctuation. Each of the punctuation defines that the Q string before the punctuation is not a sub-string of the entire long string minus the last character made up by all characters before the punctuation. Thereby, the complexity is calculated as 8.
5. Set a heart-rate threshold TDR and complexity thresholds LCT, MCT, and HCT, and directly determine a ventricular fibrillation or a ventricular tachycardia based on the calculated heart rate and complexity, as shown in the flow chart of FIG. 1.

In the prior art as described above, there are the following disadvantages:

(1) The calculation according to the given algorithm is complicated This is mainly reflected by the complicated calculation of heart rate and lots of times the character string are compared during the calculation of complexity.

(2) This detection method directly determines a ventricular fibrillation through analysis of heart rate and complexity. In practice, however, it may easily lead to wrong judgment since ventricular tachycardia, superventricular tachycardia, AF and AFL all may involve high complexity.

(3) Sensitivity and specificity are both low. That is mainly because it does not accurately differentiate the cases of ventricular fibrillation (VF), ventricular tachycardia (VT), atrial fibrillation (AF), atrial flutter (AFL) and superventricular tachycardia (SVT) from each other, and also fails to take into consideration the influence of various noises. As a result, it falls behind the clinical needs.

SUMMARY

The present application aims at solving the above-said problem. Specifically, it is to provide a synthetic detection method for ventricular fibrillation that enables to fully satisfy the clinical needs and is more effective for use in clinical diagnoses.

As presently acknowledged by those skilled in the art, VF and VT are mainly differentiated by means of data-complexity analysis. Meanwhile, it is noted that VF, AF, AFL, SVT, etc. can be differentiated alternatively through analysis of a peak value of slope and an amplitude probability density of the signal data. Generally speaking, the slope and amplitude probability density for VF are relatively low, whereas, the slope and amplitude probability density for AF, AFL, SVT etc. are relatively high due to the presence of a complete QRS wave.

To achieve the above object, the embodiments described herein sets forth a complexity-based synthetic detection method for ventricular fibrillation, which comprises steps of:

(1) sampling a n number data samples from a ECG signal at a predetermined sampling rate;

(2) preprocessing said data sample by means of noise filtering to produce data y(n);

(3) performing amplitude standardization to amplitude value A of data y(n), thereby obtaining data $y1(n)$;

(4) calculating a slope peak value SLMax, a probability density value PD and a complexity value C(n) of the data $y1(n)$ respectively;

(5) setting respective threshold values: a complexity high threshold CHigh, a complexity low threshold CLow, a complexity medium threshold CMid, a first amplitude probability density threshold PDJ1, a second amplitude probability density threshold PDJ2, a first slope threshold SLMaxJ1 and a second slope threshold SLMaxJ2, wherein PDJ1<PDJ2, SLMaxJ1>SLMaxJ2;

(6) if C(n)>Cmid && PD<PDJ1 && SLMax<SLMaxJ1∥C(n)>Chigh && PD<PDJ2 && SLMax<SLMaxJ2∥C(n)>CLow, determining that VF occurs; otherwise, no VF occurs.

With the above detection method, the embodiments described herein are capable of to reduce the load of data processing while effectively exclude the influence of AF, AFL, SVT, etc. on the detection result of VF by incorporating analyses of the slope peak value and the amplitude probability density.

The VF synthetic detection method according to the above, further comprises a step (7): re-sampling an m number of data from the ECG-signal, eliminating the first m number of data within the n number of original data in a first-in-first-out mode, thereby forming a new n number of ECG-signal data sample for analysis. Then, it returns to steps (1)-(6) to start a new round of analysis.

The above-described technical solution produces the following benefits:

The embodiments center on complexity calculation while incorporating a plurality of feature values by means of multiple processing means, for synthetically detecting ventricular fibrillation. It can more effectively differentiate various types of ECG signals and accurately distinguishes VF from ventricular tachycardia (VT), atrial fibrillation (AF), atrial flutter (AFL) and superventricular tachycardia (SVT). It can fully satisfy the clinical needs and is highly effective for use in clinical diagnoses.

By adopting multiple means processing and incorporating a plurality of feature values for synthetically detecting ventricular fibrillation, the embodiments enhance sensitivity, specificity and anti-interference ability so that the detection result is more accurate and credible for clinical needs.

In some cases, the embodiment modifies the complexity calculation method in the prior art, enabling it more adapted to reflecting characteristics of the VF-related signals. Meanwhile, it employs a slope peak value detection method and a probability density analysis method to eliminate the interference of VT, AF etc. on VF, which realizes high sensitivity and specificity. Further, the calculation load is reduced due to abandonment of the heart-rate calculation that is less effective for the detection. Accordingly, the detection method aims to solve the problems of low sensitivity, low specificity and weak auti-interference ability present in current medical equipment for detecting ventricular fibrillation, such as monitors, implanted cardiac defibrillator (ICD), automatic external defibrillator (AED) and so on.

DETAILED DESCRIPTION

Detailed description of the embodiment is provided with reference to the accompanying drawings.

Example 1

Figure 1:
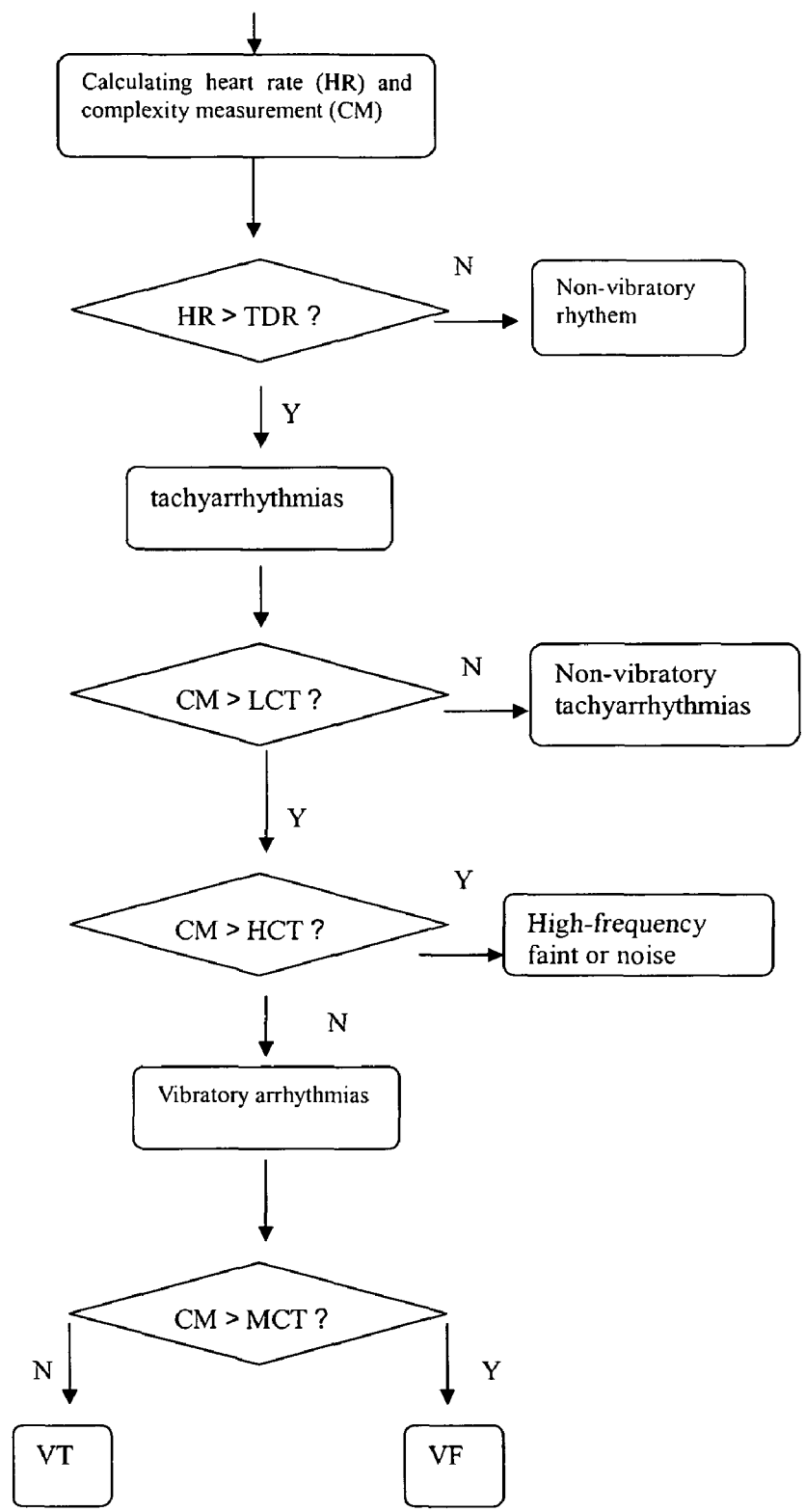
FIG. 1 is a flow chart of the complexity-based VF detection method in the prior art.
Figure 2A:
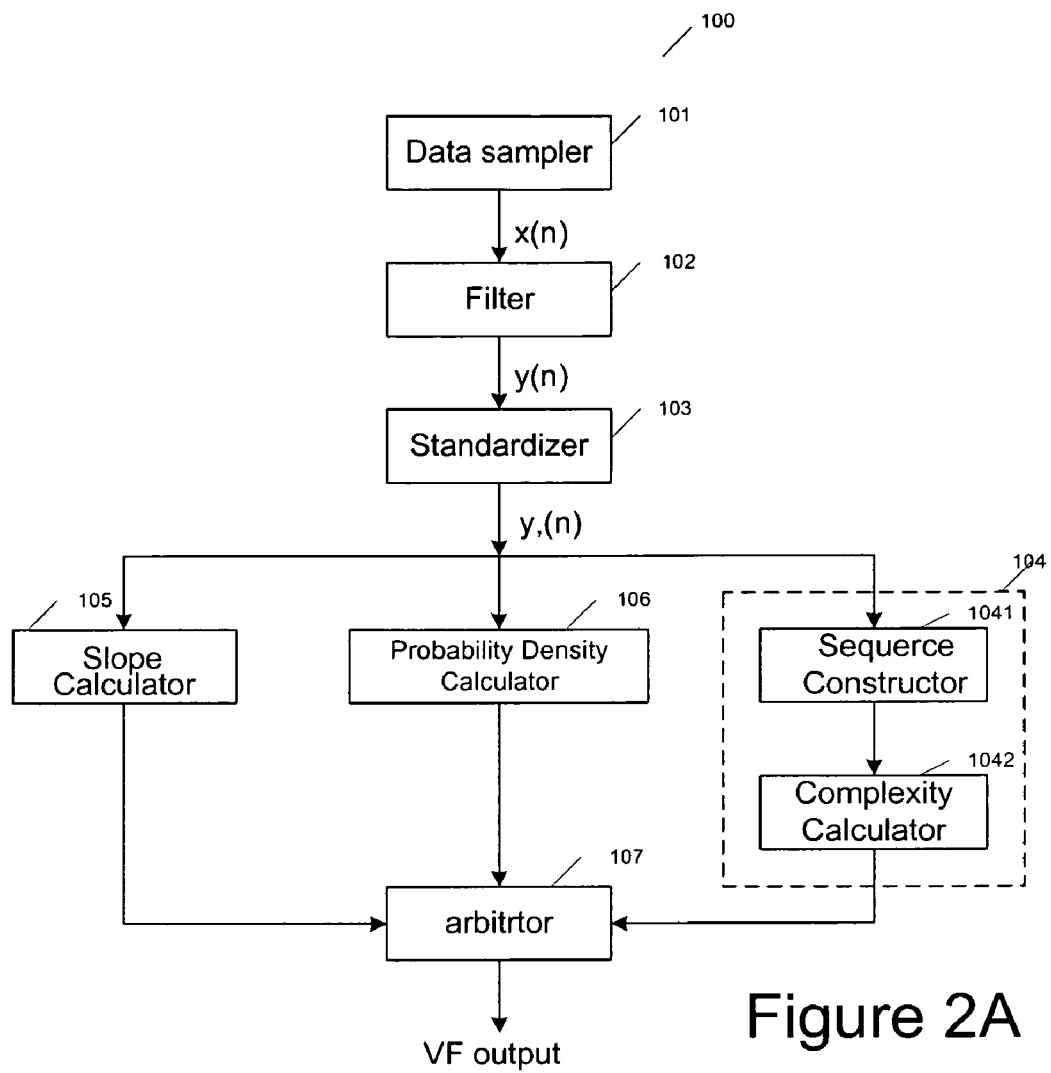
FIG. 2A is a block diagram of the VF detection apparatus according to an embodiment.

FIG. 2A is a block diagram of the VF detection apparatus according to an embodiment. As shown in the figure, the VF detection apparatus 100 comprises a data sampler 101, a high-pass filter 102, a standardizer 103, a complexity calculation device 104, an amplitude probability density calculator 106, a slope calculator 105 and an arbitrator 107.

In this architecture, the data sampler 101 serves to collect n number of data samples over a predetermined time from the ECG data signals, which is recorded as X(n).

Figure 3:
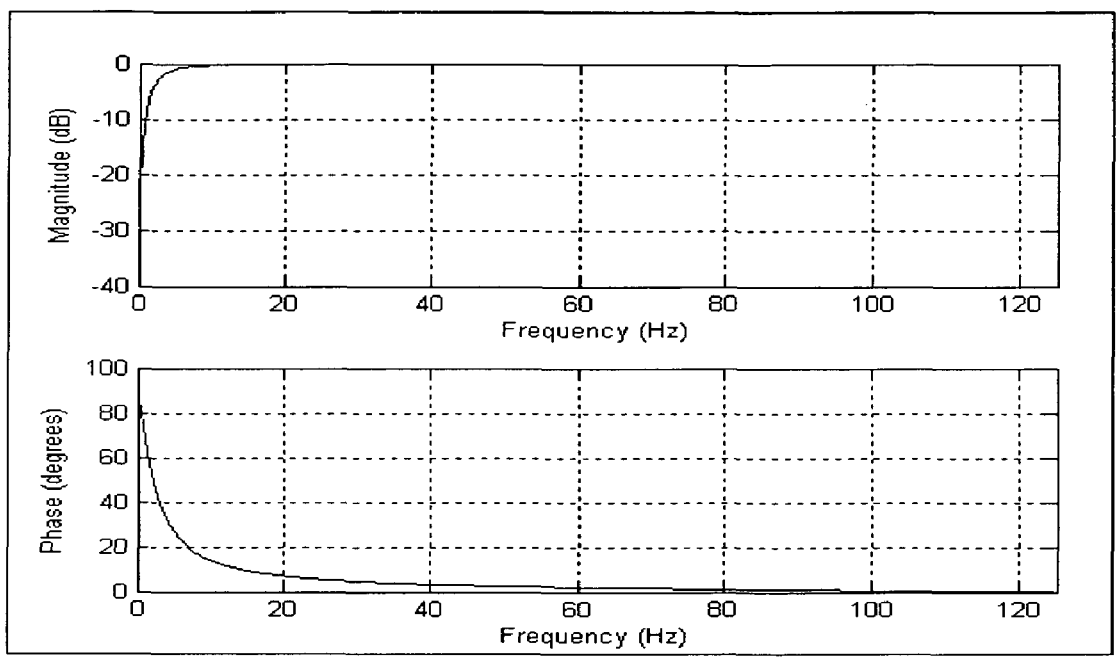
FIG. 3 shows a phase characteristics graph of the high-pass filter employed in the present embodiment.

The low noise filter 102 is used for applying high-pass filtering to data samples received from the data sampler 101 so as to obtain data y(n) in which a low-frequency noise is cleared off. In this embodiment, a one-order Butterworth high-pass filter with a cut-off frequency of 2.5 Hz is used to preprocess the data samples X(n) and remove the low-frequency noise thereof, wherein the amplitude and phase characteristics are shown in FIG. 3. Data y(n) is calculated by means of the following differential equation:

$$y(n)=[9695x(n)-9695x(n-1)+9391y(n-1)]/10000.$$

Amplitude standardizer 103 performs amplitude standardization to the data y(n) and thus outputs the data $y1(n)$ by means of any amplitude standardization technology well known in the prior art. In the present embodiment, the amplitude standardizer 103 executes a standardization process, which comprises:

(1) calculating a mean of the maximum amplitude values whose absolute values are less than 1000 in each respective second, represented as AmpMaxAverage; and meanwhile setting the other amplitude values whose absolute values are larger than 1000 equal to 1000;

(2) calculating a value of k according to the formula k=1000/AmpMaxAverage, and when k>2.5, setting k=2.5;

(3) multiplying each y(n) by k so as to obtain the standardized data $y1(n)$.

The data $y1(n)$ outputted from the standardizer 103 are provided to the slope calculator 105, amplitude probability calculator 106 and complexity calculation device 104 respectively. In the present embodiment, the slope calculator 105 calculates a slope of the data $y1(n)$, which comprises:

(1) calculating the slope of two samples using a differential algorithm:

$$y2(n)=|y1(n)-y1(n-1)|;$$

(2) calculating a slope peak value over each second, i.e. the maximum value of y2(n);

(3) calculating a mean of the slope peak values in each respective second, as the slope peak value SLMax (Slope-Max).

The amplitude probability density calculation executed by the amplitude probability calculator 106 comprises the following steps:

(1) obtaining the mean of the maximum amplitude values whose absolute values are less than 1000 in each respective second, called AmpMaxAverage;

(2) calculating the number r of y1(n) whose amplitude is in the range of (-AmpMaxAverage×K, +AmpMaxAverage×K), wherein K is an experiential value that is estimated and analyzed in accordance with the method recommended in the American National Standard ANSI/AAMI EC57-1998 titled "Testing and Reporting Performance Results of Cardiac Rhythm and ST Segment Measurement Algorithms", and using the international standard database MIT, CU, and AHA. In the present embodiment, K is preferably between 0.2 and 0.4, and more preferably 0.3. The probability density PD is calculated according to PD=r/n.

The complexity calculation device 104 performs a complexity calculation to the data sample y1(n), thereby obtaining a value of the complexity C(n). The calculation device disclosed in the prior ant WO0224276 can be used as the complexity calculation device in the present embodiment.

The results outputted from the slope calculator 105, amplitude probability calculator 106 and complexity calculation device 104 respectively are provided to the arbitrator 107, in which the inputted data are analyzed and judged to determine the presence of a VF. Details of the procedure are as follows.

(a) Set a first slope threshold value SLMaxJ1 and a second slope threshold value SLMaxJ2 for the VF arbitration based on SLMax, both of which are statistical parameters (experiential parameters) that are estimated and analyzed in accordance with the method recommended in the American National Standard ANSI/AAMI EC57-1998 titled "Testing and Reporting Performance Results of Cardiac Rhythm and ST Segment Measurement Algorithms", and using the international standard database MIT, CU, and AHA. In the present embodiment, the first slope threshold is preferably between 320 and 380, while the second slope threshold is preferably between 110 and 150, and it is then determined after repeated estimation and adjustment that the optimum values thereof respectively are SLMaxJ1=350 and SLMaxJ2=130.

(b) Determine a first amplitude probability density threshold value PDJ1 and a second amplitude probability density threshold value PDJ2 based on the analyzed data received from the probability analyzer 106, both of which are empiric parameters. In the present embodiment, the first amplitude probability density threshold is preferably between 0.3 and 0.5, while the second slope threshold value is preferably between 0.5 and 0.8, and it is then determined according to database estimation and analysis that the optimum values thereof respectively are PDJ1=0.4 or 0.5 and PDJ2=0.6.

(c) Set individual complexity threshold values, for example, according to data distribution and the statistical results of the complexity calculation for mass data: complexity high threshold CHigh, preferably between 20 and 25; complexity low threshold CLow, preferably between 8 and 12, and complexity medium threshold CMid, preferably between 15 and 19. It is determined based on database estimation and analysis that the optimum values thereof respectively are CHigh=23, CLow=9 and CMid=18.

(d) The arbitrator performs a synthetic determination based on the respective threshold values as analyzed such that: if C(n)>Cmid && PD<PDJ1 && SLMax<SLMaxJ1 && IsVF=False||C(n)>Chigh && PD<PDJ2 && SLMax<SLMaxJ2 && IsVF=False||C(n)>Clow && IsVF=True, then it is determined that VF occurs while setting IsVF=True; otherwise, setting IsVF=False, the value of IsVF is then stored for next usage; wherein IsVF refers to a previous indication of VF and initialized to False for the first determination. Subsequently, the arbitrator causes the data sampler to resample m samples to substitute for the first m samples in the initial n samples in a FIFO mode so that form n new samples. The new samples are then subjected to the filter 102, standardizer 103, complexity calculation device 104, amplitude probability density calculator 106, slope calculator 105 to recalculate said parameters including the slope peak value SLMax, the probability density value PD, and the complexity value C(n). The arbitrator determines VF again based on the new parameters calculated from the new samples. In such a way, the VF detection apparatus continuously samples new data and repeatedly above calculation and determination process so that the VF output are updated.

In a more preferable embodiment, the arbitrator 107 comprises a first threshold setting means 1071, a second threshold setting means 1072 and a third threshold setting means 1073 for making the above-said selections of slope threshold values, amplitude probability density threshold values and complexity threshold values. The arbitrator further includes a comparator 1074 that serves to perform the related comparisons and determinations and thus output a signal indicative of VF.

Figure 4:
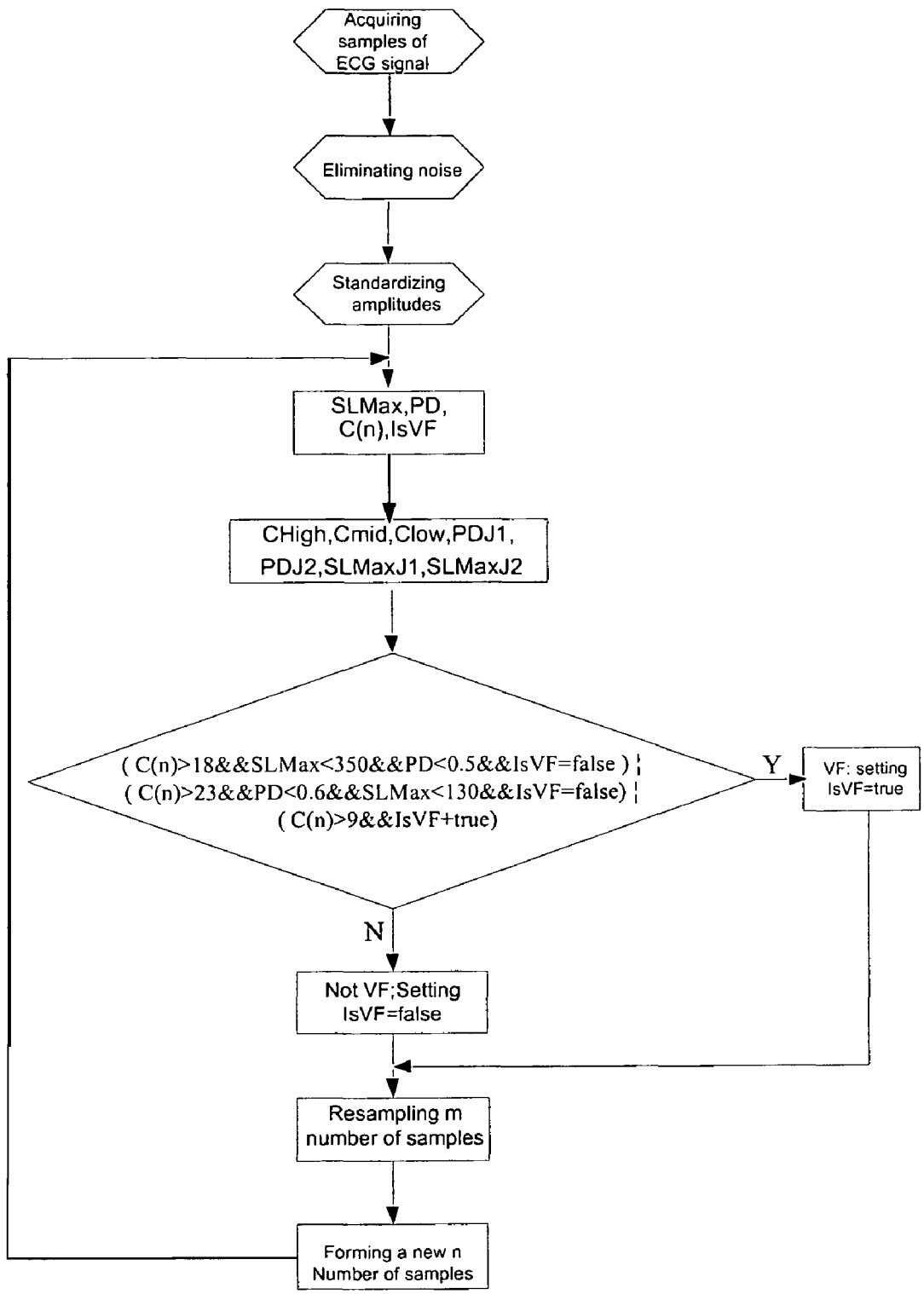
FIG. 4 is a flow chart of the synthetic detection process according to the present embodiment.

A flow chart of the VF detection process implemented by the VF detection apparatus is shown in FIG. 4.

Referring to FIG. 4, the synthetic automatic detection method, in response to the randomicity of ECG signals, the obscurity of VF, the disturbance of noise, and the highly desired detection sensitivity and specificity, first eliminates the noise in the signals, then performs a preprocessing of amplitude standardization, and finally synthesizes the respective values of complexity, amplitude probability density and maximum slope to detect VF. Details of the process are as follows.

In step S100, the data sampler samples the inputted ECG signals, for example over six second at a sampling rate of 250 Hz, as data sample X(n), which is to be recorded in a storing area with a preset fixed length. Thus the number of data samples is n=250×6.

In step S200, the Butterworth high-pass filter 102 preprocesses the samples X(n) to eliminate low-frequency noise therein and data y(n) is thus outputted.

In step S300, the amplitude standardizer 103 applies amplitude standardization to the data y(n) and obtains data y1(n), thereby proceeding to step S400.

In step S400, a value calculator, which comprises a slope peak analyzer, an amplitude probability density calculator and a complexity calculation device, calculates respectively the maximum slope SLMax (SlopeMax), the amplitude probability density PD and the complexity C(n) of the inputted data y1(n). Then it goes to step S500.

In step S500, thresholds of the respective parameters are determined, which includes the first slope threshold SLMaxJ1, the second slope threshold SLMaxJ2; the first amplitude probability density threshold PDJ1, the second amplitude probability density threshold PDJ2; complexity high threshold CHigh, complexity low threshold CLow, and complexity medium threshold CMid. In the present example, the arbitrator 107 is used for the determination of threshold and sets SLMaxJ1=350, SLMaxJ2=130, PDJ1=0.5, PDJ2=0.6, Chigh=23, Clow=9, Cmid=18. However, it is well known to those skilled in the art that the determination of the thresholds may be done respectively by the slope calculator, the amplitude probability density calculator and the complexity calculation device, and the calculated parameters and their thresholds as determined are then supplied to the arbitrator for further comparison and judgment.

In the step S600, the arbitrator determines VF as such that when [C(n)>18, PD<0.5, SLMax<350 and IsVF=False], or [C(n)>23, PD<0.6, SLMax<130 and IsVF=False], or else [C(n)>9 and IsVF=True], it is determined that VF occurs and IsVF is set to True; otherwise, IsVF=False. the set IsVF value is then stored for next usage, wherein the initial value of IsVF is set to False.

In the step S700, the data samples over the first two seconds in the initial six-second storing area are removed and the sampler re-samples m samples over another two seconds to form a new six-second data sample together with the remained samples in the storing area. Then the process repeats S200, S300, S400 and S600 for a new round of the analysis and determination of VF.

Embodiment 2

The second embodiment is substantially the same as the first. The difference lies in a complexity calculation device 104 employed in the second embodiment provided with a new-pattern complexity algorithm, which is, in substance, an improved version over the Lempel-Ziv algorithm. Further, it is noted by the inventor that since the calculation of a signal complexity requires first to perform a binary coding to the data $y1(n)$, an appropriate coding mechanism will do much favor to the algorithm-based detection.

Figure 2B:
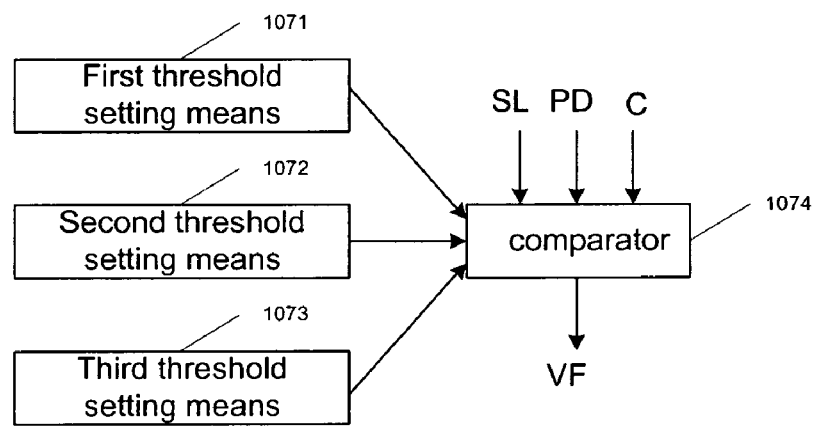
FIG. 2B shows a preferable structure of an arbitrator according to the embodiment.

As shown in FIG. 2, the complexity calculation device according to the second embodiment comprises a sequence constructor 1041 and a complexity calculator 1042, wherein the sequence constructor 1041 implements the following 0-1 coding process.

(a) Take data sample $y1(n)$ over a six-second for analysis. The sampling ratio being 250 Hz, the number of data n=6*250, and the value of each of the samples being $A_1, A_2 \ldots A_n$.

(b) Calculate a mean $A_{ave}$ of $A_1, A_2 \ldots A_n$.

(c) Calculate a maximum positive value Vpmax, and a minimum negative value Vnmax of $A_i - A_{ave}$.

(d) Calculate the number Pc of $A_i$ in the case of $0.0<A_i<10\%$ Vpmax, and the number Nc of $A_i$ in the case of $10\%$ Vnmax$<A_i<0.0$.

(e) Determine a binary threshold value Td for the data samples. When Pc+Nc<40%·n, Td=0.0; otherwise, Td=20% Vpmax when Pc<Nc, and Td=20% Vnmax when Pc>=Nc.

(f) Convert the sequence $A_1, A_2 \ldots A_n$ into 0 or 1; wherein $A_i$=1 when $A_i$>=Td, while $A_i$=0 when $A_i$<Td, thereby obtaining a binary character sequence.

After the binary conversion of data $y1(n)$, the resulted binary sequence is outputted to the complexity calculator 1042 for a complexity calculation, which comprises the steps of:

(1) defining the binary character sequence as $S_1, S_2, \ldots S_n$, S and Q being character strings of the sequence, setting $S=S_1S_2 \ldots S_r$, and $Q=S_{r+1}$, wherein r is ranging from 0 to n−1; defining the length of the Q string as Qlength, and a maximum value of the length as Qlengthmax which has an initial value of 0;

(2) designating SQ to represent a general character string concatenated by strings S and Q, and SQV to represent a sequence string resulted from deleting the last character of SQ, setting SQV=$S_1S_2 \ldots S_r$; determining whether Q is contained in SQV; wherein if Q is not contained in the SQV, then $S_{r+1}$ is added to S, i.e. $S=S_1S_2 \ldots S_rS_{r+1}$, and then C(n)=C(n)+1, Qlengthmax=Qlength=1. subsequently, Q is assigned to the next character to repeat the above processing; whereas if $Q=S_{r+1}$ is contained in SQV, it is then observed whether $Q=S_{r+1}S_{r+2}$ is contained in SQV, wherein SQV= $S_1S_2 \ldots S_rS_{r+1}$. If feasible, then The process goes on with $Q=S_{r+1}S_{r+2}S_{r+3}$.

(3) Continuing like this, the procedure may result in two possibilities:

(a) Q contains the last character Sn of the sequence, thus the process ends, (b) If any $Q=S_{r+1}S_{r+2} \ldots S_{r+i}$ is not contained in SQV, then the complexity C(n) increments, now Qlength=i. at this time the following determination is performed: if Qlength is more than or equal to the previous Qlengthmax, updating Qlengthmax=Qlength and meanwhile adding $S_{r+1}S_{r+2} \ldots S_{r+Qlength}$ to S, thereby $S=S_1S_2 \ldots S_rS_{r+1} \ldots S_{r+Qlength}$, and then proceeding to the next character $S_{r+Qlength+1}$; whereas if the Qlength is less than the previous Qlengthmax, adding $S_{r+1}S_{r+2} \ldots S_{r+1}+S_{r+i+1}+ \ldots +S_{r+i+(Qlengthmax-Qlength)}$, rather than the present $Q=S_{r+1}S_{r+2} \ldots S_{r+i}$, to the S string, thereby rendering $S=S_1S_2 \ldots S_rS_{r+1} \ldots S_{r+Qlengthmax}$, and then proceeding to the next character. As a result, the final complexity C(n) is calculated. Again, take a previously mentioned sequence 001111000011100001111001100011110001 for example. According to the complexity algorithm provided in the present embodiment, Q strings thereof are defined as 0.01.1110.0001.1100001111.00110.00111100.01, and the complexity is calculated as 7.

Compared with the Lempel-Ziv algorithm of the prior art, the algorithm is more favorable to magnifying the difference between VF-related signals and other signals in terms of their complexity levels, since each addition is conducted with respect to the maximum number of characters in all previous Q string. Meanwhile, because the number of characters during each addiction is larger than that in the Lempel-Ziv algorithm, the number of times for comparison is reduced, or in other words, the calculation load is reduced.

VF detecting device is more capable of differentiating VF from ventricular tachycardia (VT), atrial fibrillation (AF), atrial flutter (AFL) and supraventricular tachycardia (SVT) etc. It is more effective in terms of anti-interference of noise and possesses high detection sensitivity and specificity.

VF detecting device has been strictly tested with respect to the standard databases of CUDB, AHA and MIT-BIH, in accordance with Standard EC57 from the American National Standard Institute and the Associated Committee for the Development of Medical Facilities.

The configuration (method) can still produce similar effects after the following modifications thereof:

(1) values of the respective parameters for use in the 0-1 conversion in the sequence constructor, fluctuating around previously defined values, above or blow;

(2) All the threshold values fluctuating around properly, above or below;

The present embodiments can also be applied to the following products (methods): monitors, defibrillators, implanted cardioversion defibrillators (ICD) and automatic external defibrillator (AED) and so on.

The above is a detailed disclosure of the embodiments. However, it should be clear that the above-described embodiments are non-limitative. Those skilled in the art are allowed to make changes or modifications based on the above disclosure. Taking the second embodiment for example, those skilled in the art can easily anticipate that the object of the embodiments can be achieved alternatively by applying the special complexity algorithm to the binary sequence resulting from the 0-1 coding mechanism of the prior art, or by applying the complexity algorithm of the prior art to the special coding method described herein. Therefore, the scope of protection of the present invention shall be defined by the accompanying claims.

What is claimed:

1. A VF detector, comprising:
   a data sampler configured to sample a n number of samples of an ECG signal at a predetermined sampling rate;
   a filter configured to preprocess the samples so as to obtain data y(n);
   a standardizer configured to perform amplitude standardization to the data y(n) so as to obtain data $y1(n)$;
   a numeric value calculator, configured to calculate parameters including a slope peak value SLMax, a probability density value PD, and a complexity value C(n) of the data $y1(n)$; and
   an arbitrator configured to detect a VF in accordance with the calculated slope peak value SLMax, probability density value PD and complexity value C(n), respectively,
   wherein said numeric value calculator further comprises:
      a slope calculator, configured to calculate the slope peak value SLMax of said data $y1(n)$;
      a probability density calculator, configured to calculate the probability density value PD of data $y1(n)$; and
      a complexity calculation device, configured to calculate the complexity value of data $y1(n)$.

2. The VF detector according to claim 1, wherein said arbitrator further comprises:
   a first threshold setting device, for setting a first slope threshold SLMaxJ1 and a second slope threshold SLMaxJ2 based on a result of the slope calculation, wherein SLMaxJ1>SLMaxJ2;
   a second threshold setting device, for setting a first amplitude probability density threshold PDJ1 and a second amplitude probability density threshold PDJ2 based on a result of the amplitude probability density calculation, wherein SLMaxJ1>SLMaxJ2;
   a third threshold setting device, for setting a complexity high threshold CHigh, a complexity low threshold CLow, and a complexity medium threshold CMid based on a result of the complexity calculation; and
   a comparator, for comparing the individual parameters to the corresponding thresholds to determine VF.

3. The VF detector according to claim 2, wherein said complexity calculation device further comprises:
   a sequence constructor, for performing 0-1 conversion to the data $y1(n)$ so as to obtain a converted binary sequence $S_1, S_2, \ldots S_n$; defining $S=S_1 S_2 \ldots S_r$, and $Q=S_{r+1} \ldots S_{r+i}$, thereby the length of the Q string Qlength=i, wherein r denotes a position where the first character in the present Q string is located in the sequence $S_1, S_2, \ldots S_n$;
   a complexity calculator, for calculating a complexity of said sequence by:
   (a) designating SQ to represent a general character string formed of two concatenated strings S, Q, and SQV to represent a string with the last character of SQ deleted, i.e. $SQV=S_1 S_2 \ldots S_r S_{r+1} \ldots S_{r+i-1}$; and
   (b) determining whether Q is contained in SQV as follows:
   if Q is not contained in SQV, determining whether Qlength is larger than Qlengthmax, Qlengthmax being the maximum length of Q string among all previous Q strings:
      if so, adding Q to S, such that $S=S_1 S_2 \ldots S_r S_{r+1} \ldots S_{r+i}$, while Qlengthmax=Qlength=i, and the complexity C(n) increments;
      otherwise, adding Q and the subsequent Qlengthmax−Qlength characters to S, such that $S=S_1 S_1 \ldots S_r S_{r+1} \ldots S_{r+i} \ldots S_{r+i+(Qlengthmax-Qlength)}$, and the complexity C(n) increments;
   if Q is contained in the SQV, then repeating the above process to determine whether $Q=S_{r+1} \ldots S_{r+i} S_{r+i+1}$ is contained in the SQV.

4. The VF detector according to claim 3, wherein said arbitrator determines VF based on the following steps, wherein IsVF refers to a previous indication of VF and initialized to False for the first determination:
   (1) if C(n)>Cmid && PD<PDJ1 && SLMax<SLMaxJ1 && IsVF=False.parallel.C(n)>Chigh && PD<PDJ2 && SLMax<SLMaxJ2 && IsVF=False.parallel. C(n)>Clow && IsVF=True, VF is detected while setting IsVF=True; otherwise, setting IsVF=False, the value of IsVF is then stored for next usage;
   (2) said arbitrator causes the sampler to re-sample m samples to substitute for the first m samples among the n initial data samples so as to form a n number of new data samples, which is then subjected to the calculators to recalculate said parameters; and
   (3) said arbitrator determines VF based on step (1) with respect to the recalculated parameters.

* * * * *